(12) United States Patent
Arlt et al.

(10) Patent No.: US 7,981,827 B2
(45) Date of Patent: Jul. 19, 2011

(54) CHIRAL PHOSPHANES FOR USE IN ASYMMETRIC SYNTHESES

(75) Inventors: Dieter Arlt, Lemgo (DE); Benjamin Meseguer, Tarragona (ES)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/578,904

(22) Filed: Oct. 14, 2009

(65) Prior Publication Data

US 2010/0099902 A1 Apr. 22, 2010

Related U.S. Application Data

(62) Division of application No. 10/940,785, filed on Sep. 14, 2004, now Pat. No. 7,625,443.

(30) Foreign Application Priority Data

Sep. 16, 2003 (DE) .................................. 103 42 672

(51) Int. Cl.
*B01J 21/00* (2006.01)
*B01J 23/00* (2006.01)
*B01J 25/00* (2006.01)
*B01J 29/00* (2006.01)
*B01J 31/00* (2006.01)
*B01J 27/00* (2006.01)

(52) U.S. Cl. ......... 502/162; 502/100; 502/150; 502/208

(58) Field of Classification Search .................. 502/162, 502/100, 150, 208
See application file for complete search history.

(56) References Cited

U.S. PATENT DOCUMENTS

| | | | |
|---|---|---|---|
| 4,556,740 A * | 12/1985 | Hansen et al. | 568/13 |
| 4,879,416 A * | 11/1989 | Puckette et al. | 568/13 |
| 5,110,955 A * | 5/1992 | Knierzinger et al. | 549/411 |
| 6,521,769 B1 * | 2/2003 | Zhang | 556/19 |
| 7,625,443 B2 * | 12/2009 | Arlt et al. | 106/435 |
| 2001/0056210 A1 * | 12/2001 | Pugin et al. | 564/317 |

FOREIGN PATENT DOCUMENTS

| | | |
|---|---|---|
| EP | 0749973 | 11/2001 |
| EP | 1002801 | 6/2003 |
| WO | WO 01/21625 | 3/2001 |
| WO | WO 2004031110 | 4/2004 |

OTHER PUBLICATIONS

Grushin, V. "Synthesis of Hemilabile Phosphine-Phosphine Oxide Ligands via the Highly selective Pd-Catalyzed Mono-Oxidation of Bidentate Phosphines: Scope, Limitations, and Mechanism" Organometallics, 20:3950-3961 (2001).

Schmid, R. et al. "102.Axially Dissymmetric Bis(triaryl)phosphines in the Biphenyl Series: Synthesis of (6,6'-Dimethylbiphenyl-2,2'-diyl)bis(diphenylphosphine) ('BIPHEMP') and Analogues, and their Use in Rh(I)-Catalyzed Asymmetric Isomerizations of N,N-Diethylnerylamine" Helvetica Chimica Acta, 71:897-929 (1988).

Noyori, R., et al. "Asymmetrische Katalyse mit hinsichtlich Struktur und Funktion gezielt entworfenen Molekulen: die chemo- und stereoselektive Hydrierung von Ketonen", Agnew. Chem., 113:40-75 (2001).

Schmid, R., et al. "New Developments in Enantioselective Hydrogenation", Pure & Applied Chemistry, Pergamon Press, Oxford, GB, Bd. 68, Nr. 1, 1996, Seiten 131-138, XP000884387, ISSN: 0033-4545, das ganze Dokument.

Zhang, X., et al. "Highly Enantioselective Hydrogenation of a,β-Unsaturated Carboxylic Acids Catalyzed by $H_8$-BINAP-Ru(II) Complexes" Synlett, Letters, pp. 501-503 (Jul. 1994).

Noyori, R., et al. "BINAP: An Efficient Chiral Element for Asymmetric Catalysis" Acc. Chem. Res., 23:345-350 (1990).

* cited by examiner

*Primary Examiner* — Jerry Lorengo
(74) *Attorney, Agent, or Firm* — Michael P. Morris; Mary-Ellen M. Devlin

(57) ABSTRACT

The present invention relates to biarylbisphosphines and intermediates thereof. Furthermore, the scope of the invention encompasses catalysts which can be prepared from the bisarylphosphines and their use in asymmetric syntheses.

10 Claims, No Drawings

CHIRAL PHOSPHANES FOR USE IN ASYMMETRIC SYNTHESES

The present invention relates to biarylbisphosphines and intermediates thereof. Furthermore, the scope of the invention encompasses catalysts which can be prepared from the bisarylphosphines and their use in asymmetric syntheses.

Enantiomerically enriched biarylbisphosphines, particularly those derived from substituted binaphthyls and biphenyls, when used as ligands in transition metal catalyst complexes often lead to good to very good enantioselectivity (cf., for example, Helv. Chim. Acta 1988, 71, 897-929; Acc. Chem. Res. 1990, 23, 345-350; Synlett 1994, 501-503; Angew. Chem. 2001, 113, 40-75).

Steric and electronic factors which are determined by the type and arrangement of substituents on the biaryl system or within the phosphine groups influence both the enantioselectivity and the activity of the catalysts prepared from such ligands.

In individual cases, Rh and Ru catalysts of this type are used industrially for enantioselective C=C double bond isomerizations and for enantioselective hydrogenations. The number of such industrial processes has hitherto been restricted because the number of available ligands which can successfully be used broadly for a large number of substrates is small. Rather, the comprehensive studies in this field show that, owing to the substrate specificity which is an in-principle property of the catalyst which is often "tailored" for a very specific substrate, even slight changes within the same substrate group does not allow the required enantiomeric purity to be achieved for a very similar product.

EP-A 643 065 and EP-A 749 973 disclose representatives of biphenylbisphosphines which are substituted in the 5,5' and 6,6' positions and which enable the catalysts obtainable from these ligands to be matched to particular substrates by varying the phosphane substituents, so that optimized enantioselectivities are achieved.

However, there continues to be a need to provide a group of ligands and catalysts which can be prepared therefrom which make possible both a generally high level of enantioselectivity and activity and allow matching to a particular substrate in a simple fashion by varying the substituents on the ligand system.

The present invention provides compounds of the formula (I),

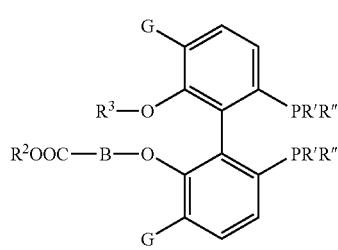

(I)

where
B is a $C_1$-$C_4$-alkylene radical which may be singly or multiply substituted by $C_1$-$C_4$-alkyl and
$R^2$ is alkyl and
$R^3$ is alkyl or B—$COOR^2$ and
G is chlorine or hydrogen, preferably chlorine, and
R' and R" are each, independently of one another, aryl or alkyl.

The invention encompasses both stereoisomerically enriched compounds of the formula (I) and also optically inactive mixtures of compounds of the formula (I). Optically inactive mixtures of compounds of the formula (I) are, in particular, racemic mixtures or, if diastereomers are present, mixtures of racemic mixtures.

Preference is given to stereoisomerically enriched compounds of the formula (I) which have a molar stereoisomer purity of 90% and more, particularly preferably 95% or more and very particularly preferably 99% or more. In the case of compounds of the formula (I) which can occur in two enantiomeric forms, preference is accordingly given to an ee of 80% or more, particularly preferably an ee of 90% or more and very particularly preferably an ee of 98% or more. At a molar stereoisomer purity of 99.5% and more or an enantiomer purity of 99% ee or more, the terms stereoisomerically pure or enantiomerically pure are used.

Within the scope of the invention, all of the radical definitions, parameters and explanations, both in general terms and in preference ranges, given above or indicated below can be combined in any way, i.e. including between the respective ranges and preference ranges.

The term alkyl refers, by way of example and preferably, to unbranched, branched, cyclic or acyclic $C_1$-$C_{12}$-alkyl radicals which may either be unsubstituted or at least partially substituted by fluorine, chlorine or unsubstituted or substituted aryl or $C_1$-$C_6$-alkoxy. The term alkyl particularly preferably refers to branched, cyclic or acyclic $C_1$-$C_{12}$-alkyl radicals which are not substituted further.

The term aryl refers, by way of example, to carbocyclic aromatic radicals having from 6 to 18 skeletal carbon atoms or heteroaromatic radicals having form 5 to 18 skeletal carbon atoms, in which no, one, two or three skeletal carbon atoms per ring, but at least one skeletal carbon atom in the total molecule, can be replaced by heteroatoms selected from the group consisting of nitrogen, sulphur and oxygen. Furthermore, the carbocyclic aromatic radicals or heteroaromatic radicals can be substituted by up to five identical or different substituents per ring selected from the group consisting of free or protected hydroxy, iodine, bromine, chlorine, fluorine, cyano, free or protected formyl, $C_1$-$C_{12}$-alkyl such as methyl, ethyl, n-propyl, isopropyl, n-butyl, text-butyl, cyclohexyl, n-hexyl, n-octyl or isooctyl, $C_6$-$C_{12}$-aryl, for example phenyl, $C_1$-$C_6$-alkoxy, tri($C_1$-$C_6$-alkyl)siloxyl, for example trimethylsiloxyl, triethylsiloxyl and tri-n-butylsiloxyl.

Examples of carbocyclic aromatic radicals having from 6 to 18 skeletal carbon atoms are phenyl, naphthyl, phenanthrenyl, anthracenyl and fluorenyl, heteroaromatic radicals having from 5 to 18 skeletal carbon atoms in which no, one, two or three skeletal carbon atoms per ring but at least one skeletal carbon atom in the total molecule can be replaced by heteroatoms selected from the group consisting of nitrogen, sulphur and oxygen, for example pyridinyl, oxazolyl, thienyl, benzofuranyl, benzothienyl, dibenzofuranyl, dibenzothienyl, furanyl, indolyl, pyridazinyl, pyrazinyl, pyrimidinyl, thiazolyl, triazolyl or quinolinyl.

For the purposes of the present invention, protected formyl is a formyl radical which has been protected by conversion into an aminal, acetal or a mixed aminal-acetal, where the aminals, acetals and mixed aminal-acetals can be acyclic or cyclic.

For the purposes of the invention, protected hydroxy is a hydroxy radical which has been protected by conversion into an acetal, carbonate, carbamate or carboxylate. Examples are conversion into a tetrahydropyranyl adduct or into a benzyloxycarbonyl, allyloxycarbonyl or tert-butyloxycarbonyl derivative.

The preference ranges for compounds of the formula (1) are defined below.

B is preferably $CHR^1$, where $R^1$ is hydrogen or $C_1$-$C_4$-alkyl, preferably hydrogen or methyl.

$R^2$ is preferably methyl, ethyl, n-propyl, isopropyl, n-butyl or tert-butyl.

$R^3$ is preferably $C_1$-C6-alkyl or $CHR^1$—$COOR^2$, particularly preferably cyclohexyl, methoxycarbonylmethyl, ethoxycarbonylmethyl, n-propoxycarbonylmethyl, isopropoxycarbonylmethyl, n-butoxycarbonylmethyl and tert-butylcarbonylmethyl, 1-methoxycarbonylethyl, 1-ethoxycarbonylethyl, 1-n-propoxycarbonylethyl, 1-isopropoxycarbonylethyl, 1-n-butoxycarbonylethyl and 1-tert-butoxycarbonylethyl.

When $R^3$ is a radical of the B—$COOR^2$ type, this radical is preferably identical with the second radical of the B—$COOR^2$ type.

R' and R" are preferably each, independently of one another, more preferably identical to one another, $C_5$-$C_8$-alkyl or $C_5$-$C_{10}$-aryl which is unsubstituted, monosubstituted or polysubstituted by radicals selected from the group consisting of chlorine, fluorine, cyano, phenyl, $C_1$-$C_6$-alkoxy and $C_1$-$C_6$-alkyl, particularly preferably cyclopentyl, cyclohexyl, cycloheptenyl, phenyl, o-, m-, p-tolyl, 3,5-dimethylphenyl, 3,5-di-tert -butylphenyl, 3,5-dimethyl-4-methoxyphenyl, 3,5-di-tert-butyl-4-methylphenyl, 4-trifluoromethylphenyl, 4-fluorophenyl, 2-, 3-furyl, 2-, 3-thienyl, 2-N-methylpyrrolyl, N-methyl-2-indolyl and 2-thiazolyl.

Particularly preferred compounds of the formula (1) are:

(R)- and (S)-[5,5'-dichloro-6,6'-bis(1-methoxycarbonylethoxy)biphenyl-2,2'-diyl]bis[(diphenyl)phosphine], (R)- and (S)-[5,5'-dichloro-6,6'-bis(1-ethoxycarbonylethoxy)biphenyl-2,2'-diyl]bis[(diphenyl)phosphine], (R)- and (S)-[5,5'-dichloro-6,6'-bis(methoxycarbonylmethoxy)biphenyl-2,2'-diyl]bis[(diphenyl)phosphine], (R)- and (S)-[5,5'-dichloro-6,6-bis(1-ethoxycarbonylmethoxy)biphenyl-2,2'-diyl]bis[(diphenyl)phosphine], (R)- and (S)-[5,5'-dichloro-6-(methoxycarbonylmethoxy)-6'-(cyclohexyloxy)biphenyl-2,2'-diyl]bis[(diphenyl)phosphine], (R)- and (S) -[5,5'-dichloro-6-(ethoxycarbonylmethoxy)-6'-(cyclohexyloxy)biphenyl-2,2'-diyl]bis[(diphenyl)phosphine], (R)- and (S)-[5,5'-dichloro-6,6'-bis(1-methoxycarbonylethoxy)biphenyl-2,2'-diyl]bis[(dicyclohexyl)phosphine], (R)- and (S)-[5,5'-dichloro-6,6'-bis(ethoxycarbonylethoxy)biphenyl-2,2'-diyl]-bis[(dicyclohexyl)phosphine], (R)- and (S)-[5,5'-dichloro-6,6'-bis(methoxycarbonylmethoxy)biphenyl-2,2'-diyl]bis[(dicyclohexyl)phosphine], (R)- and (S)-[5,5'-dichloro-6,6'-bis(ethoxycarbonylmethoxy)biphenyl-2,2'-diyl]bis[(dicyclohexyl)phosphine], (R)- and (S)-[5,5'-dichloro-6-(methoxycarbonylmethoxy)-6'-(cyclohexyloxy)biphenyl-2,2'-diyl]bis[(dicyclohexyl)phosphine], (R)- and (S)-[5,5'-dichloro-6-(ethoxycarbonylmethoxy)-6'-(cyclohexyloxy)biphenyl-2,2'-diyl]bis-[(dicyclohexyl)phosphine], (R)- and (S)-[5,5'-dichloro-6,6'-bis(1-methoxycarbonylethoxy)biphenyl-2,2'-diyl]bis[(di-3,5-di-tert-butyl-4-methoxyphenyl)phosphine], (R)- and (S)-[5,5'-dichloro-6,6'-bis(1-ethoxycarbonylethoxy)-biphenyl-2,2'-diyl]bis[(di-3,5-di-tert-butyl-4-methoxyphenyl)phosphine], (R)- and (S)-[5,5'-dichloro-6,6'-bis(methoxycarbonylmethoxy)biphenyl-2,2'-diyl]bis[(di-3,5-di-tert-butyl-4-methoxyphenyl)phosphine], (R)- and (S)-[5,5'-dichloro-6,6'-bis(ethoxycarbonylmethoxy)biphenyl-2,2'-diyl]bis[(di-3,5-di-tert-butyl-4-methoxyphenyl)phosphine], (R)- and (S)-[5,5'-dichloro-6-(methoxycarbonylmethoxy)-6'-(cyclohexyloxy)biphenyl-2,2'-diyl]bis[(di-3,5-di-tert-butyl-4-methoxyphenyl)phosphine], (R)- and (S)-[5,5'-dichloro-6-(ethoxycarbonylmethoxy)-6'-(cyclohexyloxy)biphenyl-2,2'-diyl]bis[(di-3,5-di-tert-butyl-4-methoxyphenyl)phosphine], (R)- and (S)-[5,5'-dichloro-6,6'-bis(1-methoxycarbonylethoxy)biphenyl-2,2'-diyl]bis[(di-3,5-dimethyl-4-methoxyphenyl)phosphine], (R)- and (S)-[5,5'-dichloro-6,6'-bis(1-ethoxycarbonylethoxy)biphenyl-2,2'-diyl]bis[(di-3,5-dimethyl-4-methoxyphenyl)phosphine], (R)- and (S)-[5,5'-dichloro-6,6'-bis(methoxycarbonylmethoxy)biphenyl-2,2'-diyl]bis[(di-3,5-dimethyl-4-methoxyphenyl)phosphine], (R)- and (S)-[5,5'-dichloro-6,6'-bis(ethoxycarbonylmethoxy)biphenyl-2,2'-diyl]bis[(di-3,5-dimethyl-4-methoxyphenyl)phosphine], (R)- and (S)-[5,5'-dichloro-6-(methoxycarbonylmethoxy)-6'-(cyclohexyloxy)biphenyl-2,2'-diyl]bis[(di-3,5-dimethyl-4-methoxyphenyl)phosphine], (R)- and (S)-[5,5'-dichloro-6-(ethoxycarbonylmethoxy)-6'-(cyclohexyloxy)biphenyl-2,2'-diyl]bis[(di-3,5-dimethyl-4-methoxyphenyl)phosphine], (R)- and (S)-[5,5'-dichloro-6,6'-bis(1-methoxycarbonylethoxy)biphenyl-2,2'-diyl]bis[(di-3,5-di-tert-butylphenyl)phosphine], (R)- and (S)-[5,5'-dichloro-6,6'-bis(1-ethoxycarbonylethoxy)biphenyl-2,2'-diyl]bis[(di-3,5-di-tert-butylphenyl)phosphine], (R)- and (S)-[5,5'-dichloro-6,6'-bis(methoxycarbonylmethoxy)biphenyl-2,2'-diyl]bis[(di-3,5-di-tert-butylphenyl)phosphine], (R)- and (S)-[5,5'-dichloro-6,6'-bis(ethoxycarbonylmethoxy)biphenyl-2,2'-diyl]bis[(di-3,5-di-tert-butylphenyl)phosphine], (R)- and (S)-[5,5'-dichloro-6-(methoxycarbonylmethoxy)-6'-(cyclohexyloxy)biphenyl-2,2'-diyl]bis[(di-3,5-di-tert-butylphenyl)phosphine], (R)- and (S)-[5,5'-dichloro-6-(ethoxycarbonylmethoxy)-6'-(cyclohexyloxy)biphenyl-2,2'-diyl]bis[(di-3,5-di-tert-butylphenyl)phosphine], (R)- and (S)-[5,5'-dichloro-6,6'-bis(1-methoxycarbonylethoxy)biphenyl-2,2'-diyl)]is[(di-4-fluoro-phenyl)phosphine], (R)- and (S)-[5,5'-dichloro-6,6'-bis(1-ethoxycarbonylethoxy)biphenyl-2,2'-diyl]bis[(di-4-fluorophenyl)phosphine], (R)- and (S)-[5,5'-dichloro-6,6'-bis(methoxycarbonylmethoxy)biphenyl-2,2'-diyl]bis[(di-4-fluorophenyl)phosphine], (R)- and (S)-[5,5'-dichloro-6,6'-bis(ethoxycarbonylmethoxy)biphenyl-2,2'-diyl]bis[(di-4-fluorophenyl)phosphine], (R)- and (S)-[5,5'-dichloro-6-(methoxycarbonylmethoxy)-6'-(cyclohexyloxy)biphenyl-2,2'-diyl]bis[(di-4-fluorophenyl)phosphine)] and also (R)- and (S)-[5,5'-dichloro-6-(ethoxycarbonylmethoxy)-6'-(cyclohexyloxy)biphenyl-2,2'-diyl]bis[di-fluorophenyl)phosphine], and also the analogous compounds which are unsubstituted in the 5,5' positions and in the case of a sterogenic centre in the radicals bound in the 6 and/or 6' position also the corresponding compounds having (R) and (S) configurations in the radicals mentioned.

The novel compounds of the formula (I) can be prepared, for example, by in a step a)

converting compounds of the formula (II)

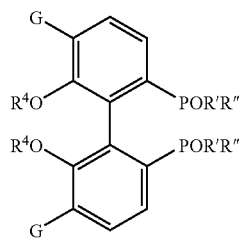

(II)

by ether cleavage into compounds of the formula (III),

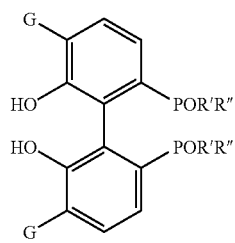

(III)

in a step b1), reacting the compounds of the formula (III) with compounds of the formula (IV)

R³-Akt          (IV)

in the presence of base to form compounds of the formula (V),

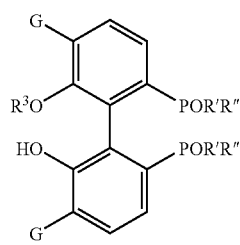

(V)

in a step b2)

reacting the compounds of the formula (V) with compounds of the formula (VI)

R²OOC—B-Akt     (VI)

in the presence of base to form compounds of the formula (VII),

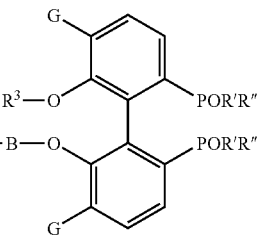

(VII)

and, in a step c), reducing the compounds of the formula (VII) to compounds of the formula (I), where B, R², R³, G, R' and R" in the formulae mentioned have the same meanings and preference ranges as have been defined above under the formulae (I) and (II) and Akt is halogen or a sulphonate, preferably chlorine or bromine, particularly preferably bromine, and R⁴ in the formula (II) is $C_1$-$C_6$-alkyl.

If the compounds of the formulae (IV) and (V) which are used are identical, the steps b1) and b2) are of course preferably carried out in one reaction.

If compounds of the formula (II) which are not already enantiomerically enriched are used for preparing compounds of the formula (I), the compounds of the formula (VII) are preferably resolved into the stereoisomers in a manner known per se, for example by reaction with a chiral auxiliary reagent or by continuous or batchwise chromatography on a chiral column material in the case of enantiomers.

The ether cleavage in step a) can, for example, be carried out in a manner known per se by reaction with $BBr_3$ and subsequent treatment with water.

The reaction of the compounds of the formula (III) with compounds of the formula (IV) in step b1) and also the reaction of the compounds of the formula (V) with compounds of the formula (VI) in step b2) are preferably carried out in organic solvents in the presence of bases.

Suitable solvents are, in particular, alcohols such as methanol, ethanol, propanol, ethylene glycol or ethylene glycol monomethyl ethyl and amide solvents such as N,N-dimethylformamide, N,N-dimethylacetamide or N-methylpyrrolidone or mixtures of the solvents mentioned.

As bases, it is possible to use, for example, alkali metal and alkaline earth metal compounds such as oxides, hydroxides, carbonates or alkoxides; examples which may be mentioned are calcium oxide, sodium hydroxide, potassium carbonate and sodium methoxide. It is also possible to use tertiary amines such as triethylamine or tributylamine as bases.

The molar ratio of the compound of the formula (III) or (V) used to the compound of the formula (IV) or (VI) is preferably from 1:1 to 1:1.5 or from 1:2 to 1:1.0 in the case of identical compounds of the formulae (IV) and (VI); a slight excess of compounds of the formula (IV) or (VI) is generally sufficient for complete reaction. The base is preferably used in at least the equivalent amount relative to the compound of the formula (III) or (V). When bases which are insoluble in the solvent are used, for example potassium carbonate in DMF, it is advantageous to use a four- to ten-fold molar amount and at the same time ensure intensive mixing of the suspension.

The reaction in step b) can also be carried out in a two-phase system using solvents in which the resulting product of the formula (V) or (VII) is at least mostly soluble as nonaqueous phase. An example of a suitable solvent is dichloromethane. It is advantageous in this variant of the reaction to use phase transfer catalysts such as quaternary ammonium or phosphine salts and tetrabutylammonium salts. Preference is given to tetrabutylammonium salts.

The reaction temperature in the reaction of compounds of the formula (III) to produce the compounds of the formula (IV) can, for example, be in the range from about 20° C. to 100° C., preferably in the range from 20° C. to 80° C. An analogous situation applies in the reaction of compounds of the formula (V) to produce the compounds of the formula (VII).

The reduction of the compounds of the formula (VII) to the compounds of the formula (I) in step c) is preferably carried out by methods known per se, for example by reaction with trichlorosilane in inert solvents such as toluene or xylene and in the presence of tertiary amines such as tri-n -butylamine at reflux temperature (cf., for example, EP-A 398 132, EP-A 749 973 and EP-A 926 152).

It is also possible in principle to carry out the reaction of compounds of the formula (III) with compounds of the formula (VI) first and subsequently react the product with compounds of the formula (IV).

The above-described process for preparing compounds of the formula (VII) and (I) is likewise encompassed by the invention, as are the compounds of the formulae (V) and (VII) necessary for the preparation of compounds of the formula (I), both in the form of their pure stereoisomers and also in any mixtures thereof, in particular a racemic mixture.

As compounds of the formula (VII), mention may be made of
(R)- and (S)-[5,5'-dichloro-6,6'-bis(1-methoxycarbonylethoxy)biphenyl-2,2'-diyl]bis[(diphenyl)phosphine oxide], (R)- and (S)-[5,5'-dichloro-6,6'-bis(1-ethoxycarbonylethoxy)biphenyl-2,2'-diyl]bis[(diphenyl)phosphine oxide], (R)- and (S)-[5,5'-dichloro-6,6'-bis(methoxycarbonylmethoxy)biphenyl-2,2'-diyl]bis[(diphenyl)phosphine oxide], (R)- and (S)-[5,5'-dichloro-6,6'-bis(1-ethoxycarbonylmethoxy)biphenyl-2,2'-diyl]bis[(diphenyl)phosphine oxide], (R)- and (S)-[5,5'-dichloro-6-(methoxycarbonylmethoxy)-6'-(cyclohexyloxy)biphenyl-2,2'-diyl]bis[(diphenyl)phosphine oxide], (R)- and (S)-[5,5'-dichloro-6-(ethoxycarbonylmethoxy)-6'-(cyclohexyloxy)biphenyl-2,2'-diyl]bis[(diphenyl)phosphine oxide],
(R)- and (S)-[5,5'-dichloro-6,6'-bis(1-methoxycarbonylethoxy)biphenyl-2,2'-diyl]bis[(dicyclohexyl)phosphine oxide], (R)- and (S)-[5,5'-dichloro-6,6'-bis(1-ethoxycarbonylethoxy)biphenyl-2,2'-diyl]bis[(dicyclohexyl)phosphine oxide], (R)- and (S)-[5,5'-dichloro-6,6'-bis(methoxycarbonylmethoxy)biphenyl-2,2'-diyl]bis[(dicyclohexyl)phosphine oxide], (R)- and (S)-[5,5'-dichloro-6,6'-bis(ethoxycarbonylmethoxy)biphenyl-2,2'-diyl]bis[(dicyclohexyl)phosphine oxide], (R)- and (S)-[5,5'-dichloro-6-(methoxycarbonylmethoxy)-6'-(cyclohexyloxy)biphenyl-2,2'-diyl]bis-[(dicyclohexyl)phosphine oxide], (R)- and (S)-[5,5'-dichloro-6-(ethoxycarbonylmethoxy)-6'-(cyclohexyloxy)biphenyl-2,2'-diyl]bis[(dicyclohexyl)phosphine oxide],
(R)- and (S)-[5,5"-dichloro-6,6-bis(1-methoxycarbonylethoxy)biphenyl-2,2'-diyl]bis[(di-3,5-di-tert-butyl-4-methoxyphenyl)phosphine oxide], (R)- and (S)-[5,5'-dichloro-6,6'-bis(1-ethoxycarbonylethoxy)biphenyl-2,2'-diyl]bis[(di-3,5-di-tert-butyl-4-methoxyphenyl) phosphine oxide], (R)- and (S)-[5,5'-dichloro-6,6-bis(methoxycarbonylmethoxy)biphenyl-2,2'-diyl]bis[(di-3,5-tert-butyl-4-methoxyphenyl)phosphine oxide], (R)- and (S)-[5,5'-dichloro-6,6'-bis(ethoxycarbonylmethoxy)biphenyl-2,2'-diyl]bis[(di-3,5-di-tert-butyl-4-methoxyphenyl)phosphine oxide], (R)- and (S)-[5,5'-dichloro-6-(methoxycarbonylmethoxy)-6'-(cyclohexyloxy)biphenyl-2,2'-diyl]bis[(di-3,5-di-tert-butyl-4-methoxyphenyl) phosphine oxide], (R)- and (S)-[5,5'-dichloro-6-(ethoxycarbonylmethoxy)-6'-(cyclohexyloxy)biphenyl-2,2'-diyl]bis[(di-3,5-di-tert-butyl-4-methoxyphenyl) phosphine oxide],
(R)- and (S)-[5,5'-dichloro-6,6'-bis(1-methoxycarbonylethoxy)biphenyl-2,2'-diyl]bis[(di-3,5-dimethyl-4-methoxyphenyl)phosphine oxide], (R)- and (S)-[5,5'-dichloro-6,6'-bis(1-ethoxycarbonylethoxy)biphenyl-2,2'-diyl]bis[(di-3,5-dimethyl-4-methoxyphenyl)phosphine oxide], (R)- and (S)-[5,5'-dichloro-6,6-bis(methoxycarbonylmethoxy)biphenyl-2,2'-diyl]bis[(di-3,5-dimethyl-4-methoxyphenyl)phosphine oxide], (R)- and (S)-[5,5'-dichloro-6,6-bis(ethoxycarbonylmethoxy)biphenyl-2,2'-diyl]bis[(di-3,5-dimethyl-4-methoxyphenyl)phosphine oxide], (R)- and (S)-[5,5'-dichloro-6-(methoxycarbonylmethoxy)-6'-(cyclohexyloxy)biphenyl-2,2'-diyl]bis[(di-3,5-dimethyl-4-methoxyphenyl)phosphine oxide], (R)- and (S)-[5,5'-dichloro-6-(ethoxycarbonylmethoxy)-6'-(cyclohexyloxy)biphenyl-2,2'-diyl]bis[(di-3,5-dimethyl-4-methoxyphenyl)phosphine oxide],
(R)- and (S)-[5,5'-dichloro-6,6'-bis(1-methoxycarbonylethoxy)biphenyl-2,2'-diyl]bis[(di-3,5-di-tert-butylphenyl)phosphine oxide], (R)- and (S)-[5,5'-dichloro-6,6'-bis (1ethoxycarbonylethoxy)biphenyl-2,2'-diyl]bis[(di-3,5-di-tert-butylphenyl)phosphine oxide], (R)- and (S)-[5,5'-dichloro-6,6-bis(methoxycarbonylmethoxy)biphenyl-2,2'-diyl]bis[(di-3,5-di-tert-butylphenyl)phosphine oxide], (R)- and (S)-[5,5'-dichloro-6,6'-bis(ethoxycarbonylmethoxy)biphenyl-2,2'-diyl]bis[(di-3,5-di-tert-butylphenyl)phosphine oxide], (R)- and (S)-[5,5'-dichloro-6-(methoxycarbonylmethoxy)-6'-(cyclohexyloxy)biphenyl-2,2'-diyl]bis[(di-3,5-di-tert-butylphenyl)phosphine oxide], (R)- and (S)-[5,5'-dichloro-6-(ethoxycarbonylmethoxy)-6 '-(cyclohexyloxy)biphenyl-2,2'-diyl]bis[(di-3,5-di-tert-butylphenyl)phosphine oxide],
(R)- and (S)-[5,5'-dichloro-6,6'-bis(1-methoxycarbonylethoxy)biphenyl-2,2'-diyl]bis[(di-4-fluorophenyl)phosphine oxide], (R)- and (S)-[5,5'-dichloro-6,6'-bis(1-ethoxycarbonylethoxy)biphenyl-2,2'-diyl]bis[(di-4-fluorophenyl)phosphine oxide], (R)- and (S)-[5,5'-dichloro-6,6'-bis(methoxycarbonylmethoxy)biphenyl-2,2'-diyl]bis[(di-4-fluorophenyl)phosphine oxide], (R)- and (S)-[5,5'-dichloro-6,6'-bis(ethoxycarbonylmethoxy)biphenyl-2,2'-diyl]bis[(di-4-fluorophenyl)phosphine oxide], (R)- and (S)-[5,5'-dichloro-6-(methoxycarbonylmethoxy)-6'-(cyclohexyloxy)biphenyl-2,2'-diyl]bis[(di-4-fluorophenyl)phosphine oxide] and also (R)- and (S)-[5,5'-dichloro-6-(ethoxycarbonylmethoxy)-6'-(cyclohexyloxy) biphenyl-2,2'-diyl]bis[(di-4-fluorophenyl)phosphine oxide], and also the analogous compounds which are unsubstituted in the 5,5' positions and in the case of a sterogenic centre in the radicals bound in the 6 and/or 6' position also the corresponding compounds having (R) and (S) configurations in the radicals mentioned.

As compounds of the formula (V), mention may be made of
(R)- and (S)-[5,5dichloro-6-(1-methoxycarbonylethoxy)-6'-hydroxybiphenyl-2,2'-diyl]bis[(diphenyl)phosphine oxide], (R)- and (S)-[5,5'-dichloro-6-(methoxycarbonylmethoxy)-6'-hydroxybiphenyl-2,2'-diyl]bis[(diphenyl) phosphine oxide], (R)- and (S)-[5,5'-dichloro-6-(1-ethoxycarbonylethoxy)-6'-hydroxybiphenyl-2,2'-diyl]bis [(diphenyl)phosphine oxide], (R)- and (S)-[5,5'-dichloro-6-(ethoxycarbonylmethoxy)-6'-hydroxybiphenyl-2,2'-diyl]bis[(diphenyl)phosphine oxide], (R)- and (S)-[5,5'- dichloro-6-cyclohexyloxy-6'-hydroxybiphenyl-2,2'-diyl]
bis[(diphenyl)phosphine oxide],
(R)- and (S)-[5,5'-dichloro-6-(1-methoxycarbonylethoxy)-6'-hydroxybiphenyl-2,2'-diyl]bis[(dicyclohexyl)phosphine oxide], (R)- and (S)-[5,5'-dichloro-6-(methoxycarbonylmethoxy)-6'-hydroxybiphenyl-2,2'-diyl]bis[(dicyclohexyl)phosphine oxide], (R)- and (S)-[5,5'-dichloro-6-(1-ethoxycarbonylethoxy)-6'-hydroxybiphenyl-2,2'-diyl]bis[(dicyclohexyl)phosphine oxide], (R)- and (S)-[5,5'-dichloro-6-(ethoxycarbonylmethoxy)-6'-hydroxybiphenyl-2,2'-diyl]bis[(dicyclohexyl)phosphine oxide], (R)- and (S)-[5,5'-dichloro-6-cyclohexyloxy-6'-hydroxybiphenyl-2,2'-diyl]bis[(dicyclohexyl)phosphine oxide],
(R)- and (S)-[5,5'-dichloro-6-(1-methoxycarbonylethoxy)-6'-hydroxybiphenyl-2,2'-diyl]bis[(di-3,5-di-tert-butyl-4-methoxyphenyl)phosphine oxide], (R)- and (S)-[5,5'-dichloro-6-(methoxycarbonylmethoxy)-6'-hydroxybiphenyl-2,2'-diyl]bis[(di-3,5-di-tert-butyl-4-methoxyphenyl)phosphine oxide], (R)- and (S)-[5,5'-dichloro-6-(1-ethoxycarbonylethoxy)-6'-hydroxybiphenyl-2,2'-diyl]bis[(di-3,5-di-tert-butyl-4-methoxyphenyl)phosphine oxide], (R)- and (S)-[5,5'-dichloro-6-(ethoxycarbonylmethoxy)-6'-hydroxybiphenyl-2,2'-diyl]bis[(di-3,5-di-tert-butyl-4-methoxyphenyl)phosphine oxide], (R)- and (S)-[5,5'-dichloro-6-cyclohexyloxy-6'-hydroxybiphenyl-2,2'-diyl]bis[(di-3,5-di-tert-butyl-4-methoxyphenyl)phosphine oxide],
(R)- and (S)-[5,5'-dichloro-6-(1-methoxycarbonylethoxy)-6'-hydroxybiphenyl-2,2'-diyl]bis[(di-3,5-methyl-4-methoxyphenyl)phosphine oxide], (R)- and (S)-[5,5'-dichloro-6-(methoxycarbonylmethoxy)-6'-hydroxybiphenyl-2,2'-diyl]bis[(di-3,5-methyl-4-methoxyphenyl)phosphine oxide], (R)- and (S)-[5,5'-dichloro-6-(1-ethoxycarbonylethoxy)-6'-hydroxybiphenyl-2,2'-diyl]bis[(di-3,5-methyl-4-methoxyphenyl)phosphine oxide], (S)- and (S)-[5,5'-dichloro-6-(ethoxycarbonylmethoxy)-6'-hydroxybiphenyl-2,2'-diyl]bis[(di-3,5-methyl-4-methoxyphenyl)phosphine oxide], (R)- and (S)-[5,5'-dichloro-6-cyclohexyloxy-6'-hydroxybiphenyl-2,2'-diyl]bis[(di-3,5-methyl-4-methoxyphenyl)phosphine oxide],
(R)- and (S)-[5,5'-dichloro-6-(1-methoxycarbonylethoxy)-6'-hydroxybiphenyl-2,2'-diyl]bis[(di-3,5-di-tert-butylphenyl)phosphine oxide], (R)- and (S)-[5,5'-dichloro-6-(methoxycarbonylmethoxy)-6'-hydroxybiphenyl-2,2'-diyl]bis[(di-3,5-di-tert-butylphenyl)phosphine oxide], (R)- and (S)-[5,5'-dichloro-6-(1-ethoxycarbonylethoxy)-6'-hydroxybiphenyl-2,2'-diyl]bis[(di-3,5-di-tert-butylphenyl)phosphine oxide], (R)- and (S)-[5,5'-dichloro-6-(ethoxycarbonylmethoxy)-6'-hydroxybiphenyl-2,2'-diyl]bis[(di-3,5-di-tert-butylphenyl)phosphine oxide], (R)- and (S)-[5,5'-dichloro-6-cyclohexyloxy-6'-hydroxybiphenyl-2,2'-diyl]bis[(di-3,5-di-tert-butylphenyl)phosphine oxide],
(R)- and (S)-[5,5'-dichloro-6-(1-methoxycarbonylethoxy)-6'-hydroxybiphenyl-2,2'-diyl]bis[(di-4-fluorophenyl)phosphine oxide], (R)- and (S)-[5,5'-dichloro-6-(methoxycarbonylmethoxy)-6'-hydroxybiphenyl-2,2'-diyl]bis[(di-4-fluorophenyl)phosphine oxide], (R)- and (S)-[5,5'-dichloro-6-(1-ethoxycarbonylethoxy)-6'-hydroxybiphenyl-2,2'-diyl]bis[(di-4-fluorophenyl)phosphine oxide], (R)- and (S)-[5,5'-dichloro-6-(ethoxycarbonylmethoxy)-6'-hydroxybiphenyl-2,2'-diyl]bis[(di-4-fluorophenyl)phosphine oxide], (R)- and (S)-[5,5'-dichloro-6-cyclohexyloxy-6'-hydroxybiphenyl-2,2'-diyl]bis[(di-4-fluorophenyl)phosphine oxide], and also the analogous compounds which are unsubstituted in the 5,5' positions and in the case of a sterogenic centre in the radicals bound in the 6 and/or 6' position also the corresponding compounds having (R) and (S) configurations in the radicals mentioned.

The compounds of the formula (I), preferably in stereoisomerically enriched form, are particularly suitable as ligands for the preparation of transition metal complexes which can be used as catalysts for processes for preparing enantiomerically enriched compounds.

The preference ranges for compounds of the formula (I) apply in the following in the same way as described above.

The invention therefore encompasses both transition metal complexes containing compounds of the formula (I) and also catalysts containing the transition metal complexes of the invention.

Preferred transition metal complexes are ones which are obtainable by reacting compounds of the formula (I) with transition metal compounds.

Preferred transition metal compounds are compounds of rhodium, iridium, ruthenium, palladium and nickel, and more preferably compounds of rhodium, iridium and ruthenium.

Preferred transition metal compounds are, for example, those of the formula (VIIIa)

$$M(Y^1)_3 \qquad (VIIIa)$$

where
M is ruthenium, rhodium, iridium, and
$Y^1$ is chloride, bromide, acetate, nitrate, methanesulphonate, trifluoromethanesulfonate or acetylacetonate,
or transition metal compounds of the formula (VIIIb)

$$M(Y^2)_p B^1_2 \qquad (VIIIb)$$

where
M is ruthenium, rhodium, iridium, and
$Y^2$ is chloride, bromide, acetate, methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate and
p is 1 in the case of rhodium and iridium and
is 2 in the case of ruthenium,
$B^1$ is in each case a $C_2$-$C_{12}$-alkene such as ethylene or cyclooctene or a nitrile such as acetonitrile, benzonitrile or benzyl nitrile, or
$B^1_2$ together represent a ($C_4$-$C_{12}$)-diene such as norbornadiene or 1,5-cyclooctadiene,
or transition metal compounds of the formula (VIIIc)

$$[MB^2Y^1_2]_2 \qquad (VIIIc)$$

where
M is ruthenium and
$B^2$ is an aryl radical such as cymene, mesityl, phenyl or cyclooctadiene, norbornadiene or methylallyl,
or transition metal compounds of the formula (VIIId)

$$Me_3[Mg(Y^3)_4] \qquad (VIIId),$$

M is iridium or rhodium and
$Y^3$ is chloride or bromide and
Me is lithium, sodium potassium, ammonium or organic ammonium,
or transition metal compounds of the formula (VIIIe)

$$[M(B^3)_2]An \qquad (VIIIe),$$

where
M is iridium or rhodium and
$B^3$ is a ($C_4$-$C_{12}$)-diene such as norbornadiene or 1,5-cyclooctadiene, An is a noncoordinating or weakly coordinating anion such as methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate.

Further preferred transition, metal compounds are cyclopentadienyl$_2$Ru, Rh(acac)(CO)$_2$, Ir(pyridine)$_2$(1,5-cyclooctadiene) and multinuclear bridged complexes such as [Rh(1,5-cyclooctadiene)Cl]$_2$ and [Rh(1,5-cyclooctadiene)Br]$_2$, [Rh(ethene)$_2$Cl]$_2$, [Rh(cyclooctene)$_2$Cl]$_2$, [Ir(1,5-cyclooctadiene)Cl]$_2$ and [Ir(1,5-cyclooctadiene)Br]$_2$, [Ir(ethene)$_2$Cl]$_2$, and [Ir(cyclooctene)$_2$Cl]$_2$.

Transition metal compounds which are very particularly preferably used are:
[Rh(cod)Cl]$_2$, [Rh(cod)$_2$Br], [Rh(cod)$_2$]ClO$_4$, [Rh(cod)$_2$]BF$_4$, [Rh(cod)$_2$]PF$_6$, [Rh(cod)$_2$]OTf, [Rh(cod)$_2$]BAr$_4$ (Ar=3,5-bistrifluoromethylphenyl) [Rh(cod)$_2$]SbF$_6$ RuCl$_2$ (cod), [(cymene)RuCl$_2$]$_2$, [(benzene)RuCl$_2$]$_2$, [(mesityl)RuCl$_2$]$_2$, [(cymene)RuBr$_2$]$_2$, [(cymene)RuI$_2$]$_2$, [(cymene)Ru(BF$_4$)$_2$]$_2$, [(cymene)Ru(PF$_6$)$_2$]$_2$, [(cymene)Ru(BAr$_4$)$_2$]$_2$, (Ar=3,5-bistrifluoromethylphenyl), [(cymene)Ru(SbF$_6$)$_2$]$_2$, [Ir(cod)$_2$Cl)$_2$], [Ir(cod)$_2$]PF$_6$, [Ir(cod)$_2$]ClO$_4$, [Ir(cod)$_2$]SbF$_6$ [Ir(cod)$_2$]BF$_4$, [Ir(cod)Otf], [Ir(cod)$_2$]BAr$_4$ (Ar=3,5-bistrifluoromethylphenyl) RuCl$_3$, RhCl$_3$, [Rh(nbd)Cl]$_2$, [Rh(nbd)$_2$Br], [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoromethylphenyl) [Rh(nbd)$_2$]SbF$_6$ RuCl$_2$(nbd), [Ir(nbd)$_2$]PF$_6$, [Ir(nbd)$_2$]ClO$_4$, [Ir(nbd)$_2$]SbF$_6$ [Ir(nbd)$_2$]BF$_4$, [Ir(nbd)$_2$]OTf, [Ir(nbd)$_2$]BAr$_4$ (Ar=3,5-bistrifluoromethylphenyl), Ir(pyridine)$_2$(nbd), RuCl$_3$, [Ru(DMSO)$_4$Cl$_2$], [Ru(CH$_3$CN)$_4$Cl$_2$], [Ru(PhCN)$_4$Cl$_2$], [Ru(cod)Cl$_2$]$_n$, [Ru(cod)(methallyl)$_2$] and [Ru(acetylacetonate)$_3$].

Particularly preferred transition metal complexes are those of the formulae (Xa,b,c)

[M(I)Hal]$_2$ (IXa)

[M(cod)(I)]An (IXb)

[M(nbd)(I)]An (IXc)

where
M is rhodium or iridium and
Hal is chloride, bromide or iodide and
(I) is a compound of the formula (I) and
An is a noncoordinating or weakly coordinating anion such as methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate, and
Compounds of the formulae (Xa,b,c,d,e,f)

[Ru(AcO)$_2$(I)] (Xa)

[Ru$_2$Cl$_4$(I)$_2$NEt$_3$] (Xb)

[RuHal(I)(AR)]$_2$ (Xc)

[Ru(I)](An)$_2$ (Xd)

[{RuHal(I)}$_2$(μ-Hal)$_3$]$^-$[(R''')$_2$NH$_2$]$^+$ (Xe)

[RuHal$_2$(I)(diamine)] (Xf)

where
Hal is chloride, bromide or iodide and
(I) is a compound of the formula (I) and
An is a noncoordinating or weakly coordinating anion such as methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate and
the radicals R''' are each, independently of one another, $C_1$-$C_6$-alkyl and
diamine is a chiral 1,2-diamine which is preferably selected from the group consisting of (S,S)- and (R,R)-1,2-diphenylethylenediamine and (R)- or (S)-1,1-bis(4-methoxyphenyl)-3-methyl-1,2-butanediamine, and
AR is an arene ligand which is preferably selected from the group consisting of benzene, p-cymene and mesitylene.

The preparation of such types of complexes is known in principle and can be carried out, for example, by methods analogous to those described in Chemistry Letters, 1851, 1989; J. Organomet. Chem., 1992, 428, 213 (IXa,b,c); J. Chem. Soc., Chem. Commun., 922, 1985 (Xa,b,c,d), EP-A 945 457 (Xe) and Pure Appl. Chem., Vol. 71,8,1493-1501, 1999 (Xf).

The transition metal complexes and catalysts are particularly suitable for use in a process for the transition metal-catalyzed preparation of enantiomerically enriched compounds and for C=C double bond isomerization, which is likewise encompassed by the invention.

Here, it is possible to use both isolated transition metal complexes, for example ones of the formula (IXa-c) and (Xa-e) and also transition metal complexes prepared in situ, with the latter being preferred.

The transition metal complexes and catalysts are preferably used for asymmetric hydrogenations. Preferred asymmetric hydrogenations are, for example, hydrogenations of prochiral C=C bonds, for example prochiral enamines, olefins, enol ethers, C=O bonds, for example prochiral ketones, and C=N bonds, for example prochiral imines. Particularly preferred asymmetric hydrogenations are hydrogenations of prochiral ketones, in particular alpha- and beta-keto esters such as acetoacetates or chloroacetates.

The amount of transition metal compound used or transition metal complex used can be, for example, from 0.001 to 5 mol %, based on the substrate used, preferably from 0.01 to 2 mol %.

The enantiomerically enriched compounds which can be prepared according to the invention are particularly useful for the preparation of agrochemicals, pharmaceuticals or intermediates thereof.

The advantage of the present invention is that the catalysts of the invention make it possible to achieve enantioselectivities and activities which have hitherto not been able to be achieved using similar catalysts.

EXAMPLES

Example 1

Preparation of (S)-[5,5'-dichloro-6,6-dihydroxybiphenyl-2,2'-diyl]bis(diphenylphosphine oxide)

3.4 ml of BBr$_3$ (=8.77 g) were added dropwise while stirring to a solution of 8 g of (S)-[5,5'-dichloro-6,6'-dimethoxybiphenyl-2,2'-diyl]bis(diphenylphosphine oxide) in 160 ml of methylene chloride which had been dried over CaH$_2$ and cooled to −78° C. in a stirred vessel with exclusion of moisture, and the reaction mixture was maintained at this temperature for one hour. The temperature was then allowed to rise to room temperature over a period of 2 hours and the mixture was stirred for another 24 hours at this temperature. While cooling in ice, a total of 50 ml of water were subsequently added dropwise over a period of 1 hour while mixing well, the methylene chloride was then distilled off and, after addition of a further 110 ml of water, the mixture was stirred at 80° C. for 6 hours. After cooling to RT, the precipitate which had formed was filtered off with suction via a glass filter flit, washed with 100 ml of water and then with 200 ml of methylene chloride with intensive mixing. Drying of the product which remained gave 6.3 g (=82% of theory) of pure (S)-[5,5'-dichloro-6,6'-dihydroxybiphenyl-2,2'-diyl]bis(diphenylphosphine oxide), m.p. 236-237° C.

Example 2a

Preparation of (8)-[5,5'-dichloro-6,6'-bis(methoxycarbonylmethoxy)biphenyl-2,2'-diyl]bis(diphenylphosphine oxide)

5 g (7.6 mmol) of the product prepared as described in Example 1 were mixed intensively with 12.6 g (91.6 mmol) of potassium carbonate in 150 ml of dimethylformamide at room temperature for one hour using an effective stirrer. 4.67 g (30.4 mmol) of methyl bromoacetate were then added and the reaction mixture was stirred at room temperature for a further 36 hours. The mixture was then filtered, the solvent was distilled off from the resulting filtrate under reduced pressure on a rotary evaporator and the residue was dissolved in 100 ml of dichloromethane. This solution was filtered through 20 g of silica gel and the solvent was subsequently removed under reduced pressure. This gave 5.61 g (92% of theory) of the (S) enantiomer of the desired compound, m.p.: 69° C.-72° C.; $[\alpha]_D$=+19° (c=1, CHCl$_3$).

Example 2b

Preparation of (S)-[5,5'-dichloro-6,6'-bis(ethoxycarbonylmethoxy)biphenyl-2,2'-diyl]-bis(diphenylphosphine oxide)

0.25 g (0.38 mmol) of the product prepared as described in Example 1 were intensively mixed with 0.21 g (1.52 mmol) of potassium carbonate in 5 ml of dimethylformamide at room temperature for one hour using an effective stirrer. 0.127 g (1.52 mmol) of ethyl bromoacetate was then added and the reaction mixture was stirred at 80° C. for a further 8 hours. The mixture was then cooled to room temperature, filtered and the solvent was distilled off from the resulting filtrate under reduced pressure on a rotary evaporator. The crude product obtained was purified by chromatography (silica gel Merck type 9385, eluant: hexane/ethyl acetate/methanol, 2:3:0.5). This gave 0.248 g of pure (S)-[5,5'-dichloro-6,6'-bis(ethoxycarbonylmethoxy)biphenyl-2,2'-diyl]bis(diphenylphosphine oxide), m.p.: 148° C.-149°; $[\alpha]_D$=+24.1° (c=1, CHCl$_3$).

Example 3

Preparation of (S)-[6-cyclohexyloxy-6'-hydroxybiphenyl-2,2'-diyl]bis(diphenylphosphine oxide) and (S)-[6-(methoxycarbonylmethoxy)-6'-(cyclohexyloxy)biphenyl-2,2'-diyl]bis(diphenylphos oxide)

Example 3a 2.6 g (4.43 mmol) of (S)-[6,6'-dihydroxybiphenyl-2,2'-diyl]bis(diphenylphosphine oxide), which can be obtained by a method fully analogous to that for the compound from Example 1, 2.44 g (17.72 mmol) of potassium carbonate and 2.71 g (17.7 mmol) of cyclohexyl bromide were mixed intensively by stirring in 30 ml of dimethylformamide at room temperature for 48 hours. The reaction mixture was subsequently filtered and the filtrate was evaporated under reduced pressure on a rotary evaporator. The product obtained was extracted three times with 50 ml each time of dichloromethane, the solution was filtered through silica gel and evaporated. This gave 3.2 g (93% of theory) of pure (S)-[6-cyclohexyloxy-6'-hydroxybiphenyl-2,2'-diyl]bis(diphenylphosphine oxide). M.p.: 91° C.-92° C.; $[\alpha]_D$=-35.2° (c=1, CHCl$_3$).

Example 3b 0.48 g (0.718 mmol) of the product obtained as described in Example 3a, 0.198 g (1.43 mmol) of potassium carbonate and 0.218 g (1.43 mmol) of methyl bromoacetate were intensively mixed by stirring in 7 ml of dimethylformamide at 80° C. for 6 hours. The resulting reaction mixture was worked up by a method analogous to that of Example 3a and the crude product obtained was purified by chromatography (silica gel Merck type 9385, eluant: ethyl acetate/methanol/water, 75:5:1). This gave 340 mg (64% of theory) of pure (S) enantiomer of the desired compound. M.p.: 104° C.-106° C., $[\alpha]_D$=-68.1° (c=1, CHCl$_3$).

Example 4

Preparation of (S)-[5,5'-dichloro-6,6'-bis(1-methoxycarbonylethoxy)biphenyl-2,2'-diyl]bis(diphenylphosphine oxide)

0.25 g (0.38 mmol) of the compound from Example 1, 0.21 g (1.52 mmol) of potassium carbonate and 0.253 g (0.152 mmol) of racemic methyl 2-bromopropionate were intensively mixed by stirring in 5 ml of dimethylformamide at 80° C. for 6 hours.

The mixture was subsequently worked up by a method analogous to that of Example 3b and the mixture of the reaction products was separated by chromatography.

This gave 2 pure stereoisomers of the formula below:
94 mg, m.p.: 201° C.-202° C., $[\alpha]_D$=-32.9" (c=0.8, CHCl$_3$), [(S)(R,R) or (S),(S,S) enantiomer].
55 mg, m.p. 108° C.-110° C., $[\alpha]_D$=-36.7° (c=0.8, CHCl$_3$), [(S)(R,S) enantiomer) and 75 mg of a mixture of these two stereoisomers.

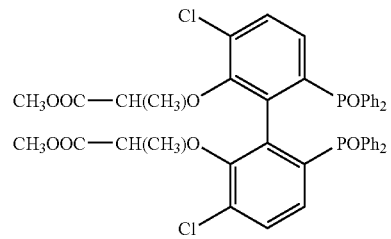

Example 5

Preparation of (S)-[5,5'-dichloro-6,6'-bis(methoxycarbonylmethoxy)biphenyl-2,2'-diyl]bis(diphenylphosphine)

The phosphine oxide from Example 2a (0.686 g, 0.86 mmol) together with xylene (18 ml) was placed under argon in a reaction vessel, and the resulting mixture was firstly admixed with tri(n-butyl)amine (3.5 ml, 15 mmol) and trichlorosilane (1.5 ml, 15 mmol) and then refluxed for 2 hours. The mixture was allowed to cool, briefly stirred with degassed NaOH solution (30%, 15 ml), 25 ml of degassed water were added and the phases were separated. The aqueous phase was extracted 3 times with methyl tert-butyl ether (10 ml) and the combined organic phases were firstly washed with saturated sodium chloride solution and then dried over $MgSO_4$. The organic solvent was removed under reduced pressure and the product was obtained as a colourless powder.

Yield: 95% of theory.

$^{31}$P-NMR: –13.4 ppm.

Example 6

Preparation of (S)-[5,5'-dichloro-6,6'-bis(ethoxycarbonylmethoxy)biphenyl-2,2'-diyl]-bis(diphenylphosphine)

The phosphine oxide from Example 2b was reduced by a method fully analogous to that of Example 5 and the product was obtained in a yield of 92%.

Example 7

Preparation of (S)-[6-(methoxycarbonylmethoxy)-6'-(cyclohexyloxy)biphenyl-2,2'-diyl]bis(diphenylphosphine)

The phosphine oxide from Example 3b was reduced by a method fully analogous to that of Example 5 and the product was obtained in a yield of 91%.

Example 8

Preparation of (S)-[5,5'-dichloro-6,6'-bis(1-methoxycarbonylethoxy)biphenyl-2,2'-diyl]bis(diphenylphosphine)

The phosphine oxide from Example 4 was reduced by a method fully analogous to that of Example 5 and the product was obtained in a yield of 94%.

Enaoselective Hydrogenation of Methyl Chloroacetate (S1)

Example 9

(S)-[5,5'-dichloro-6,6'-bis(methoxycarbonylmethoxy)biphenyl-2,2'-diyl]bis(diphenylphosphine) (5.6 mg, 0.02 mol %) from Example 5, $RuCl_3$ (1.5 mg, 0.01 mol %) and 4 g of S1 together with ethanol (10 ml) were placed in a reaction vessel and the mixture was heated at 80° C. under a hydrogen pressure of 90 bar for one hour. After this time, an enantiomeric purity of the product of 96.5% ee was determined.

Example 10

For Comparison (S)-[5,5'-dichloro-6,6'-dimethoxybiphenyl-2,2'-diyl]bis(diphenyl)phosphine (4.8 mg, 0.02 mol %), [(p-cumene)RuCl]$_2$ (1.5 mg, 0.01 mol %) and 4 g of S1 together with ethanol (10 ml) were placed in a reaction vessel and the mixture was heated at 80° C. under a hydrogen pressure of 90 bar for one hour. After this time, an enantiomeric purity of the product of 95.1% ee was determined.

Enantioselective Hydrogenation of Methyl Acetoacetate (S2)

Example 11

(S)-[5,5'-dichloro-6,6'-bis(methoxycarbonylmethoxy)biphenyl-2,2'-diyl]bis(diphenylphosphine) (5.3 mg, 0.02 mol %) from Example 5, $RuCl_3$ (1.4 mg, 0.01 mol %) and 4 g of S2 together with ethanol (10 ml) were placed in a reaction vessel and the mixture was heated at 80° C. under a hydrogen pressure of 90 bar for one hour. After this time, an enantiomeric purity of the product of 97.8% ee was determined.

Example 12

(S)-[6-(methoxycarbonylmethoxy)-6'-(cyclohexyloxy)biphenyl-2,2'-diyl]bis(diphenylphosphine) (4.9 mg, 0.02 mol %) from Example 7, $RuCl_3$ (1.4 mg, 0.01 mol %) and 4 g of S2 together with ethanol (10 ml) were placed in a reaction vessel and the mixture was heated at 80° C. under a hydrogen pressure of 90 bar for one hour. After this time, an enantiomeric purity of the product of 97.4% ee was determined.

Example 13

For Comparison (S)-[5,5'-dichloro-6,6'-dimethoxybiphenyl-2,2'-diyl]bis(diphenylphosphine) (4.5 mg, 0.02 mol %), $RuCl_3$ (1.4 mg, 0.01 mol %) and 4 g of S2 together with ethanol (10 ml) were placed in a reaction vessel and the mixture was heated at 80° C. under a hydrogen pressure of 90 bar for one hour. After this time, an enantiomeric purity of the product of 96.4% ee was determined.

We claim:

1. A compound of the formula (I),

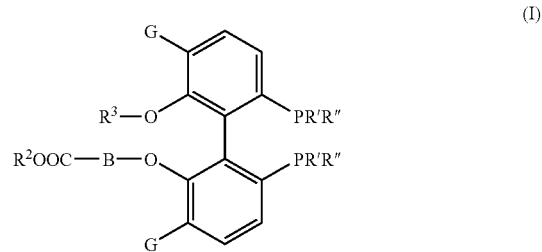

wherein:
B is a $C_1$-$C_4$-alkylene radical which may be singly or multiply substituted by $C_1$-$C_4$-alkyl;
$R^2$ is alkyl;
$R^3$ is $CHR^1$—$COOR^2$;
$R^1$ is hydrogen or $C_1$-$C_4$-alkyl;
G is chlorine or hydrogen; and
R' and R" are each, independently of one another, aryl or alkyl.

2. A compound according to claim 1, selected from the following:
(R)- and (S)-[5,5'-dichloro-6,6'-bis(1-methoxycarbonylethoxy)biphenyl-2,2'-diyl]bis[(diphenyl)phosphine],
(R)- and (S)-[5,5'-dichloro-6,6'-bis(1-ethoxycarbonylethoxy)biphenyl-2,2'-diyl]bis[(diphenyl)phosphine],
(R)- and (S)-[5,5'-dichloro-6,6'-bis(methoxycarbonylmethoxy)biphenyl-2,2'-diyl]bis[(diphenyl)phosphine],
(R)- and (S)-[5,5'-dichloro-6,6'-bis(1-ethoxycarbonylmethoxy)biphenyl-2,2'-diyl]bis[(diphenyl)phosphine], (R)- and (S)-[5,5'-dichloro-6,6'-bis(1-methoxycarbonylethoxy)biphenyl-2,2'-diyl]bis[(dicyclohexyl)phosphine],
(R)- and (S)-[5,5'-dichloro-6,6'-bis(1-ethoxycarbonylethoxy)-biphenyl-2,2'-diyl]bis[(dicyclohexyl)phosphine],
(R)- and (S)-[5,5'-dichloro-6,6'-bis-(methoxycarbonylmethoxy)biphenyl-2,2'-diyl]bis[(dicyclohexyl)phosphine],
(R)- and (S)-[5,5'-dichloro-6,6'-bis(ethoxycarbonylmethoxy)biphenyl-2,2'-diyl]bis[(dicyclohexy) phosphine],
(R)- and (S)-[5,5'-dichloro-6,6'-bis(1-methoxycarbonylethoxy)biphenyl-2,2'-diyl]bis[(di-3,5-di-tert-butyl-4-methoxyphenyl)phosphine],
(R)- and (S)-[5,5'-dichloro-6,6'-bis(1-ethoxycarbonylethoxy)biphenyl-2,2'-diyl]bis[(di-3,5-di-tert-butyl-4-methoxyphenyl)phosphine],
(R)- and (S)-[5,5'-dichloro-6,6'-bis(methoxycarbonylmethoxy)biphenyl-2,2-diyl]bis[(di-3,5-di-tert-butyl-4-methoxyphenyl)phosphine],
(R)- and (S)-[5,5'-dichloro-6,6'-bis(ethoxyearbonylmethoxy)biphenyl-2,2'-diyl]bis[(di-3,5-di-tert-butyl-4-methoxyphenyl)-phosphine],
(R)- and (S)-[5,5'-dichloro-6,6'-bis(1-methoxycarbonylethoxy)biphenyl-2,2'-diyl]bis[(di-3,5-dimethyl-4-methoxyphenyl)phosphine],
(R)- and (S)-[5,5'-dichloro-6,6'-bis(1-ethoxycarbonylethoxy)biphenyl-2,2'-diyl]bis[(di-3,5-dimethyl-4-methoxyphenyl)phosphine],
(R)- and (S)-[5,5'-dichloro-6,6'-bis(methoxycarbonyiniethoxy)biphenyi-2,2'-diyl ]bis[(di-3,5-dimethyl-4-methoxyphenyl)phosphine],
(R)- and (S)-[5,5'-dichloro-6,6'-bis(ethoxycarbonyl-methoxy)biphenyl-2,2'-diyl]bis[(di-3,5-dimethyl-4-methoxyphenyl)phosphine],
(R)- and (S)-[5,5'-dichloro-6,6'-bis(1-methoxycarbonylethoxy)biphenyl-2,2'-diyl]bis[(di-3,5-di-tert-butylphenyl)phosphine],
(R)- and (S)-[5,5'-dichloro-6,6'-bis(1-ethoxycarbonylethoxy)biphenyl-2,2'-diyi]bis[(di-3,5-di-tert-butylphenyl)phosphine],
(R)- and (S)-[5,5'-dichloro-6,6'-bis(methoxycarbonylmethoxy)biphenyl-2,2'-diyl]bis[(di-3,5-di-tert-butylphenyl)phosphine],
(R)- and (S)-[5,5'-dichloro-6,6'-bis(ethoxycarbonylinethoxy)biphenyl-2,2'-diyl]bis[(di-3,5-di-tert-butylphenyl) phosphine],
(R)- and (S)-[5,5'-dichloro-6,6'-bis(1-methoxycarbonylethoxy)biphenyl-2,2'-diyl]bis[(di-4-fluorophenyl)phosphine],
(R)- and (S)-[5,5'-dichloro-6,6'-bis(1-ethoxycarbonylethoxy)biphenyl-2,2'-diyl]bis[(di-4-fluorophenyl)phosphine],
(R)- and (S)-[5,5'-dichloro-6,6'-bis(methoxycarbonylmethoxy)biphenyl-2,2'-diyl]bis[(di-4-fluorophenyl)phosphine],
(R)- and (S)-[5,5'-dichloro-6,6'-bis(ethoxycarbonylmethoxy)biphenyl-2,2'-diyl]bis[(di-4-fluorophenyl)phosphine],
and also the analogous compounds which are unsubstituted in the 5,5' positions, and when there is a sterogenic centre in the radicals bound in the 6 and/or 6' position, the corresponding compounds having (R) and (S) configurations in the radicals mentioned.

3. A compound of the formula (VII),

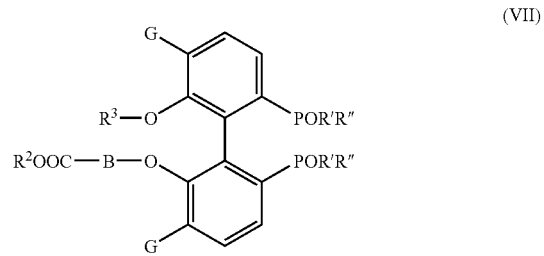

wherein:
B is a $C_1$-$C_4$-alkylene radical which may be singly or multiply substituted by $C_1$-$C_4$-alkyl;
$R^2$ is alkyl;
$R^3$ is $CHR^1$—$COOR^2$;
$R^1$ is hydrogen or $C_1$-$C_4$-alkyl;
G is chlorine or hydrogen; and
R' and R" are each, independently of one another, aryl or alkyl.

4. A compound of the formula (V):

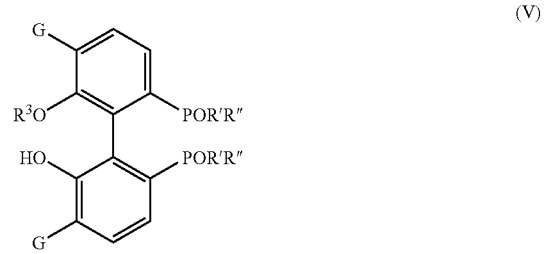

wherein:
$R^3$ is $CHR^1$—$COOR^2$;
$R^1$ is hydrogen or $C_1$-$C_4$-alkyl;
$R^2$ is alkyl;
G is chlorine or hydrogen; and
R' and R" are each, independently of one another, aryl or alkyl.

5. A composition containing a transition metal complex of a compound of the formula (I) according to claim 1.

6. The composition of claim 5, wherein the composition is a catalyst composition.

7. A compound of formula (I) of claim 1, wherein:
B is $CHR^1$;
$R^2$ is methyl, ethyl, propyl, isopropyl, n-butyl or tert-butyl;
$R^3$ is methoxycarbonylmethyl, ethoxycarbonylmethyl, n-propoxycarbonylmethyl, iso-propoxycarbonylmethyl, n-butoxycarbonylmethyl, tert.-butoxycarbonylmethyl, 1-methoxycarbonylethyl, 1-ethoxycarbonylethyl, 1-n-propoxycarbonylethyl, 1-iso-propoxycarbonylethyl, n-butoxycarbonylethyl or 1-tert.-butoxycarbonylethyl.

8. A compound of formula (I) of claim 1, wherein:
the $R^2OOC$—B— group is identical to the $R^3$ group.

9. A compound of formula (I) of claim 1, wherein:
R' and R" are, independently from one another, selected from: $C_3$-$C_8$-alkyl or $C_5$-$C_{10}$-aryl which each are substituted, monosubstituted or polysubstituted by radicals selected from the group consisting of chlorine, fluorine, cyano, phenyl, $C_1$-$C_6$-alkoxy and $C_1$-$C_6$-alkyl.

10. A compound of formula (1) of claim 1, wherein:
R' and R" are, independently from one another, selected from: cyclopentyl, cyclohexyl, cycloheptenyl, phenyl, o-, m- or p-tolyl, 3,5-dimethylphenyl, 3,5-di-tert-butylphenyl, 3,5-dimethyl-4-methoxyphenyl, 3,5-di-tert-butyl-4-methylphenyl, 4-trifluoromethylphenyl, 4-fluorophenyl, 2-, 3-furyl, 2- or 3-thienyl, 2-N-methylpyrrolyl, N-methyl-2-indolyl and 2-thiazolyl.

* * * * *